United States Patent
Koopman

(10) Patent No.: US 8,648,289 B2
(45) Date of Patent: Feb. 11, 2014

(54) DEVICE AND METHOD FOR DETECTING SMALL QUANTITIES OF LIGHT, COMPRISING AN ELECTRONIC IMAGE CONVERTER EMBODIED IN SEMICONDUCTOR TECHNOLOGY

(75) Inventor: Pieter Tjerk Koopman, Houten (NL)

(73) Assignee: Datascan Group B.V., Maarssen (NL)

( * ) Notice: Subject to any disclaimer, the term of this patent is extended or adjusted under 35 U.S.C. 154(b) by 395 days.

(21) Appl. No.: 12/743,435

(22) PCT Filed: Nov. 19, 2008

(86) PCT No.: PCT/NL2008/050734
§ 371 (c)(1), (2), (4) Date: Sep. 20, 2010

(87) PCT Pub. No.: WO2009/067006
PCT Pub. Date: May 28, 2009

(65) Prior Publication Data
US 2011/0020835 A1    Jan. 27, 2011

(30) Foreign Application Priority Data
Nov. 20, 2007 (NL) .................................... 2001016

(51) Int. Cl.
G01N 33/53 (2006.01)
H01L 27/00 (2006.01)

(52) U.S. Cl.
USPC ........................................ 250/208.1; 348/243

(58) Field of Classification Search
USPC ......... 250/208.1, 214 VT, 226; 348/307, 308, 348/243
See application file for complete search history.

(56) References Cited

U.S. PATENT DOCUMENTS

| | | | |
|---|---|---|---|
| 4,933,543 A | 6/1990 | Hull | |
| 8,076,631 B2 * | 12/2011 | Tada et al. | 250/226 |
| 2003/0107733 A1 | 6/2003 | Oka et al. | |
| 2007/0195179 A1 * | 8/2007 | Glenn et al. | 348/243 |
| 2008/0073490 A1 * | 3/2008 | Koide | 250/214 C |

FOREIGN PATENT DOCUMENTS

| | | |
|---|---|---|
| CN | 1541331 A | 10/2004 |
| DE | 10040889 A1 | 3/2002 |

OTHER PUBLICATIONS

C. Cagigal et al., Luminescence Measurements With CCDs, Proceedings of the 24th Annual Conference of the IEEE Industrial Electronics Society, 1998, pp. 1688-1693.
Khaled Salama, CMOS Luminescence Detection Lab-on-Chip: Modeling, Design, and Characterization, Ph.D. Dissertation, Stanford University, Sep. 2005, 92 pages.

* cited by examiner

Primary Examiner — Tony Ko
(74) Attorney, Agent, or Firm — The Webb Law Firm, P.C.

(57) ABSTRACT

The invention relates to a device for detecting small quantities of light, comprising an electronic image converter embodied in semiconductor technology for detecting the photons representing the small quantities of light and an electronic circuit connected to the electronic image converter for reading the electronic image converter and for generating a signal representing the number of photons received by the electronic image converter, wherein the electronic image converter comprises at least 100,000 light-sensitive cells and the electronic circuit is adapted to add together the signals coming from light-sensitive cells placed on the electronic image converter.

14 Claims, 2 Drawing Sheets

DEVICE AND METHOD FOR DETECTING SMALL QUANTITIES OF LIGHT, COMPRISING AN ELECTRONIC IMAGE CONVERTER EMBODIED IN SEMICONDUCTOR TECHNOLOGY

BACKGROUND OF THE INVENTION

1) Field of the Invention

The invention relates to a device for detecting small quantities of light, comprising optical detection means for detecting the photons representing the small quantities of light and an electronic circuit connected to the optical detection means for reading the optical detection means and for generating a signal representing the number of photons received by the optical detection means.

2) Description of the Related Art

Such devices are generally known. Such prior art detection devices make use of, among other parts, a photon multiplier tube, an expensive, heavy and fragile apparatus which requires a high supply voltage and which is therefore less suitable for use in the field.

In order to obviate these drawbacks the dissertation by Khaled Salama, Stanford University, September 2005, "Cmos-luminescence detection lab-on-chip modeling, design and characterisation", provides a device for the detection of small quantities of light, comprising an electronic image converter embodied in semiconductor technology for detecting the photons representing the small quantities of light and an electronic circuit connected to the electronic image converter for reading the electronic image converter and for generating a measurement signal representing the number of photons received by the electronic image converter.

This prior art device avoids the technical problems associated with photon multiplier tubes, such as a high supply voltage and a fragile construction.

It has however been found that, when such a device is optimized to an optimal sensitivity to light, this sensitivity is greatly influenced by the temperature. This influence is so great that the prior art device can hardly be used outside laboratory conditions. It is however the intention to use the device according to the invention in practice, i.e. outside the laboratory, at usually varying temperatures. The object of the invention is to provide such a device which—while retaining a high sensitivity to light—is as insensitive as possible to temperature.

SUMMARY OF THE INVENTION

This object is achieved with such a device which is provided with a second electronic image converter which is the same as the first electronic image converter and which is shielded from light, and wherein the processing circuit is also connected to the second electronic image converter and is adapted to compensate the readout signal of the first electronic image converter with the readout signal of the second electronic image converter, and wherein the first and the second image converters are thermally closely coupled to each other.

Both the first and the second electronic image converters are subjected to the same temperature as a result of their close thermal coupling. Because they are also as much the same as possible as each other, their output signal will comprise the same temperature-sensitive component. By shielding the second electronic image converter from light its output signal will comprise only this temperature-sensitive component, which is used according to the invention for compensation of the temperature-sensitive component of the output signal of the first electronic image converter. An output signal is hereby obtained which is insensitive to temperature to the extent that it can also be used outside laboratory situations while retaining a particularly high sensitivity to light.

The invention also relates to a method for detecting light-emitting elements present in a carrier, comprising the steps of mutually defined positioning of the carrier and a first electronic image converter, detecting the light emitted by the light-emitting elements present in the carrier, reading the first electronic image converter with a processing circuit connected to the first electronic image converter, and generating a signal representing the number of photons received by the electronic image converter within a period of time, wherein the signal is compensated with a signal coming from a second electronic image converter which is the same as the first electronic image converter and is shielded from light, but thermally closely coupled to the first electronic image converter.

Tests have shown that the light-sensitive circuit is not only sensitive to temperature variables but also to other ambient variables or external factors, such as the degree of humidity and air pressure. In order to also be able to apply as much compensation as possible for these other variables with the 'dark' image converter the first and the second image converters are placed in the vicinity of each other.

According to another preferred embodiment, the first electronic image converter comprises a first region, and the electronic circuit is adapted to read at least the light-sensitive cells placed in the first region of the image converter. The cells located outside this first region are used for compensation purposes. It is pointed out here that this reference is not intended in the first instance for compensation of temperature and other ambient variables, but for compensation of internal processes of the first image converter.

Many light measurements, in particular when extremely small quantities of light must be measured, are sensitive to outside influences. This is not only the case for the electronic part, for which the above elucidated measures provide improvements, but also for the optical part. Measurements of small quantities of light, to which the invention is applicable, relate particularly, though not exclusively, to measurements of light generated by chemical reactions. In order to also be able to equalize variations in the path between chemical reaction or other light source and the image converter, another preferred embodiment provides the measure that the device comprises a third electronic image converter which is the same as the first and the second electronic image converters and which is adapted to receive light signals functioning as comparison, that the processing circuit is also connected to the third electronic image converter and is adapted to compare the readout signal of the first electronic image converter to the readout signal of the third electronic image converter, and that the first, second and third electronic image converters are thermally closely coupled to each other. Owing to the close thermal coupling between all three image converters, they have substantially the same temperature, so that the signal coming from the 'dark' second image converter can be used to compensate the signals of the first and third image converter.

The same advantages are obtained with such a method wherein a biological sample is arranged on the carrier, the biological sample is brought into contact with a first reagent and a second reagent, the combination of the first biological sample and the first reagent forms the first light-emitting element which is positioned relative to the first electronic image converter, and the combination of the biological sample and the second reagent forms a second light-emitting element which is positioned relative to the third electronic image converter, and wherein the signals are compensated with a signal coming from a second electronic image converter which is the same as the first and third electronic image converters and shielded from light but thermally closely coupled to the first and third electronic image converters.

In order to also be able to compensate for the consequences of variations in ambient variables in the three image converters it is recommended that the first, the second and the third electronic image converters are placed in the vicinity of each other.

The light-sensitive cells present on the third image converter are preferably also divided into a measurement group and a reference group, the reference group is shielded from light and the processing circuit is adapted to compensate readout signals of the light-sensitive cells belonging to the measurement group with readout signals of light-sensitive cells belonging to the reference group.

The image converter is preferably adapted to add together for an adjustable period of time the signals coming from the light-sensitive cells of an image converter. Owing to the large number of cells use can be made of commercially available electronic image converters such as CCD detectors or CMOS detectors as are usually applied in video equipment for recording images. Image converters of other types are otherwise not excluded. These are mass-produced products with a low cost price compared to the specially designed and manufactured prior art image converters. Owing to their large number of light-sensitive cells these commercially available image converters also provide the option of greatly improving the signal/noise ratio. The signal/noise ratio does after all increase proportionally to the square root of the number of light-sensitive cells when the signals coming from the light-sensitive cells are added together. It is noted that the lower limit of 100,000 light-sensitive cells is chosen for the purpose of providing a distinction between specifically manufactured image converters and commercially available image converters normally suitable for image recording purposes; this distinction can also be set at 75,000 light-sensitive cells, 150,000 light-sensitive cells or 200,000 light-sensitive cells.

The signal/noise ratio is further improved when the image converter is adapted to add together, possibly for an adjustable period of time, the signals coming from one of the light-sensitive cells.

In order to be able to perform measurements on samples placed on a carrier it is attractive if the device is provided with positioning means for positioning a carrier so that light which is emitted by light-emitting elements placed at a first position on the carrier reaches the first electronic image converter while excluding other light. It hereby becomes possible to make comparisons between samples placed on different carriers.

In some situations it may be attractive to carry out comparisons between samples placed on the same carrier. For this purpose a preferred embodiment provides the measure that the positioning means are adapted to position a carrier so that light emitted by light-emitting elements placed at a second position on the carrier reaches the third electronic image converter while excluding other light.

The invention also relates to a carrier adapted to be positioned by the above described positioning means.

The invention further relates to a carrier adapted to add at least one reagent to the sample, and the reagent is adapted to form a light-emitting element together with cells of disease-causing micro-organisms.

For the purpose of performing comparative measurements a further preferred embodiment provides the measure that the device comprises a second image converter which is adapted to receive light emitted at a second position by light-emitting elements placed on a carrier and that the electronic circuit is adapted to read the second image converter and to compare the signals coming from the first and the second image converter. It is hereby possible to compare the quantities of light emitted by the two carriers. In a specific situation one of the samples is formed by a calibrated sample so that calibrated measurements can be carried out.

There are various possibilities for the spatial realization of this embodiment. It is thus possible for instance for both light-emitting elements to be placed on the same carrier, although it is also possible for the light-emitting elements to each be arranged on a separate carrier.

An important field of application of the invention lies in determining the extent to which samples, in particular samples of biological origin, emit light. For this purpose a specific embodiment provides the measure that the carrier is adapted to carry a light-emitting element in the form of a sample of biological origin.

Samples of biological or other origin do not usually emit any light per se, but do so when brought into contact with at least one reagent or substance. It is therefore attractive that the carrier be adapted to add at least one reagent to the sample. A specific preferred embodiment therefore provides the measure that a sample is arranged on the carrier, the sample is brought into contact with at least one substance or a reagent and that the combination of the sample and the reagent and/or the substance forms the light-emitting element.

According to a preferred embodiment, the reagent and/or the substance is adapted to form a light-emitting element together with diseased cells.

An example of a biological application is the detection and analysis of cells affected by micro-organisms. A sample is here arranged on a carrier and the sample is brought into contact with a first substance present on the carrier. This substance is for instance formed by a substance which affects the diseased cells in question, whereby ATP is released. This ATP emits photons under the influence of a reagent. It is possible to establish from the quantity of photons how much ATP is present in the sample, and thereby how many diseased cells were present in the sample.

This preferred embodiment also provides the method wherein the biological sample is formed by milk cells. The mammary glands of milk-producing animals, such as cows, sheep and goats, frequently suffer from infections such as mastitis, which renders the milk produced by these animals unusable for consumption and processing. Quite apart from the suffering of the animal, this infection results in great economic damage. Early detection and diagnosis of this infection can initiate an early treatment of this infection and thereby prevent or alleviate these drawbacks. As elucidated above, the presence in milk of cells affected by mastitis can be demonstrated and the concentration of these diseased cells can be measured. It is noted here that the biological application of the measures according to the invention is not limited to detection and quantitative analysis of mastitis, but that cells infected by other micro-organisms can also be detected and quantitatively analyzed, such as for instance cells which have been affected by micro-organisms causing urinary tract infections.

BRIEF DESCRIPTION OF THE DRAWINGS

The present invention will be elucidated hereinbelow with reference to the accompanying figures, in which.

DETAILED DESCRIPTION OF THE PREFERRED EMBODIMENTS

Figure 1:
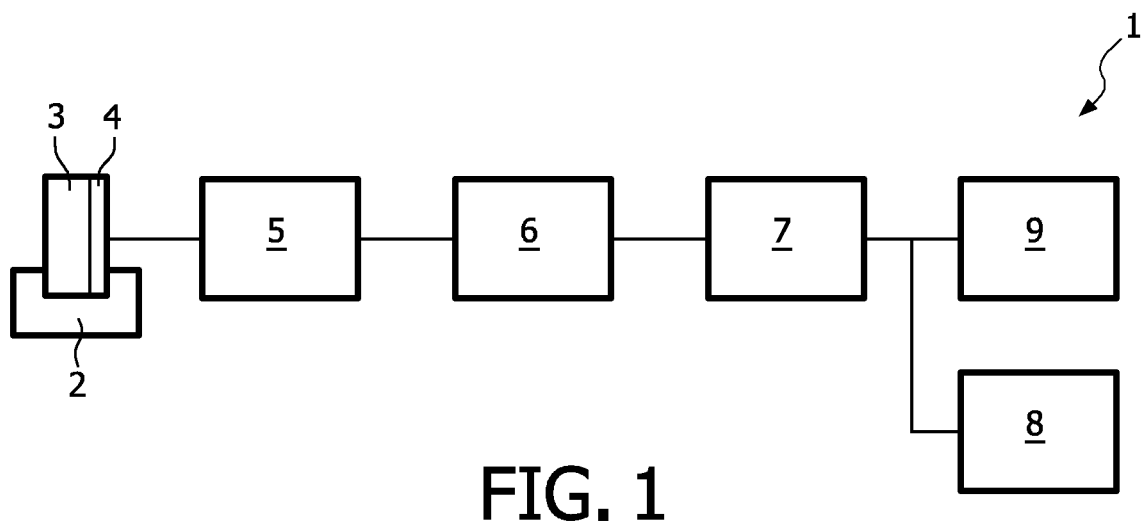
FIG. 1 shows a block diagram of an embodiment of the invention.

The block diagram of FIG. 1 shows a detection device according to the present invention, designated as a whole with 1, which is suitable for functioning as detector for small quantities of light. This detection device 1 shows a positioning element 2 for positioning a carrier 3 on which a sample 4 is arranged. When necessary, a reagent can also be arranged on carrier 3 for the purpose, in co-action with the sample, of causing or improving the light-emitting action of sample 4.

The device also comprises guide means 5, for instance in the form of a tube, optionally in combination with a filter for guiding only those parts of the spectrum which are caused by the sample placed on the carrier. The guide means lead to CCD detector 5, which is connected to an electronic circuit 7. The CCD detector is provided here with 330,000 light-sensitive elements (pixels). It is otherwise also possible to place a CMOS detector instead of a CCD detector.

Electronic circuit 7 is connected to a memory 8 for storing the measurement results, with a display 9 for displaying the measurement results and with a keyboard 10 for operating the apparatus.

Figure 2:
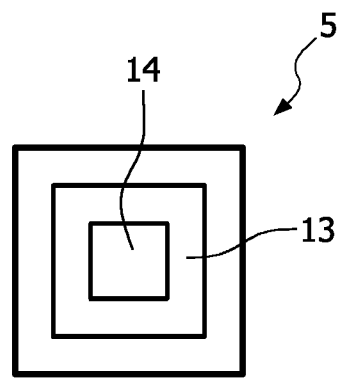
FIG. 2 shows a view of a CCD chip as part of the embodiment shown in FIG. 1.

FIG. 2 shows the CCD chip 5 on which the light-sensitive cells are arranged within a region 13. Situated within this active region 13 on CCD chip 5 is a region 14, wherein only this region 14 can be reached by the photons coming from the carrier. The part of the chip within region 13 but outside region 14 serves as compensation for the temperature dependence of the light-sensitive cells. These light-sensitive cells are here wholly shielded from the light so that their output signal represents inter alia the temperature-sensitive component.

Figure 3:
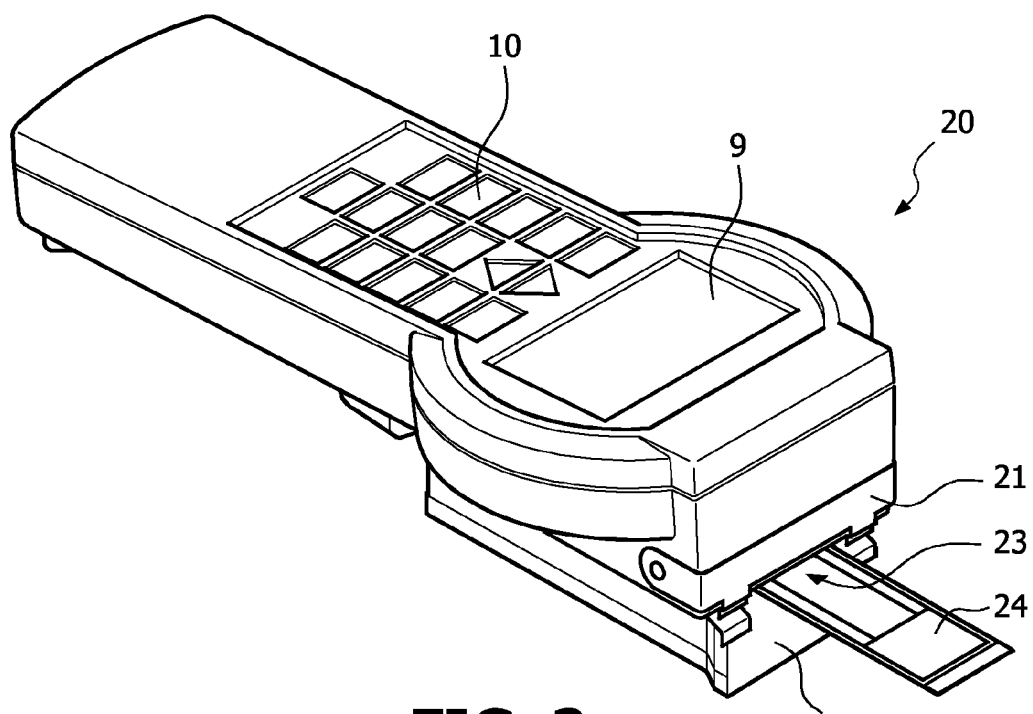
FIG. 3 is a perspective view of a measuring device according to the invention.

FIG. 3 shows an embodiment of a detection device according to the invention. This embodiment comprises a housing 20 incorporating a display 9 and a keyboard 10. Housing 20 is assembled from two divisible halves in order to gain easy access to the interior of the housing. Housing 20 is formed such that it can be held easily in the hand.

Figure 4:
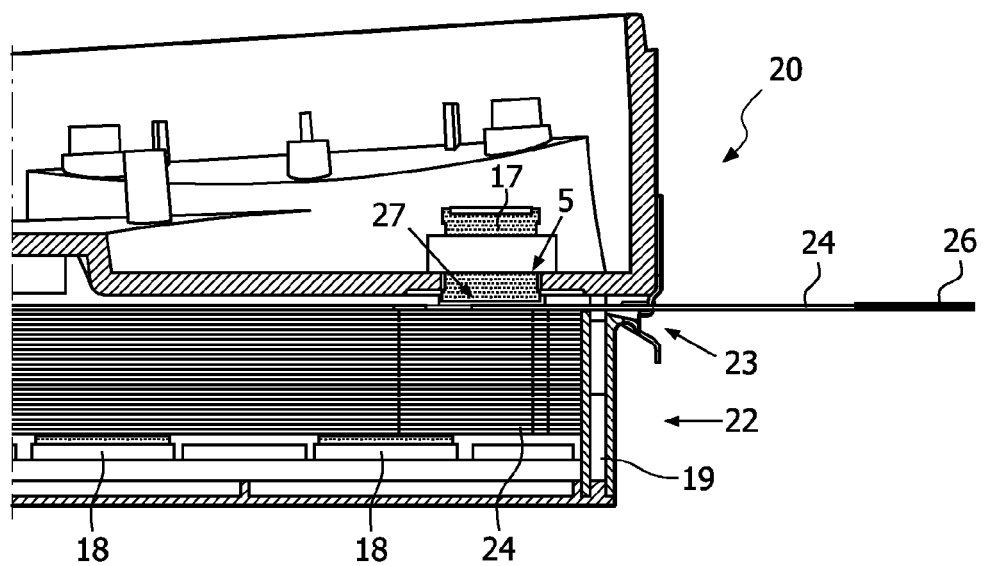
FIG. 4 is a cross-sectional view of the measuring device shown in FIG. 3.

Placed under the housing is a cassette 22 which is shown in more detail in FIG. 4. Cassette 22 comprises a slot 23 which can be closed by a movable door 19 and in which are situated a number of strip-like carriers 24 for a sample to be examined. Further arranged in cassette 22 is a transport mechanism (not shown in the drawing) which can move carriers 24 outside one by one. The carriers are pressed against the transport mechanism by springs 18.

The transport mechanism is operated by pushing one of the buttons of keyboard 10. The transport mechanism then carries the uppermost strip 24 to the position shown in FIG. 4, wherein a sample part 26 of strip 24 protrudes outside the cassette. Arranged on this sample part 26 of the carrier is a substance which selectively degrades the walls of cells affected by a micro-organism so that the ATP present in these cells is released. Carrier 24 has a capillary structure such that the released ATP comes to lie through capillary action on the measuring part 27 of carrier 24. Situated here is a reagent which emits photons together with the released ATP transported by capillary action. The measuring part 27 on which these photons are emitted is situated directly below the optical detector in the form of the CCD chip 5 of the device so that this detector 5 can determine the intensity of the photons and thereby the concentration of ATP, and thereby the concentration of the cells affected by the relevant micro-organism. It is noted that CCD detector 5 is placed in the immediate vicinity of measuring part 27 of carrier 24 in order to optimize the sensitivity. For compensation of the temperature dependence a compensating CCD chip 17 is arranged on the same carrier in order to obtain a good thermal coupling. After the measurement has been performed, the used carrier 24 is ejected, after which a new carrier becomes available.

It is also noted here that the strip preferably takes a dual form, as described above, wherein it can move and wherein a reagent which destroys all cell walls is present at a side of the location at which the liquid for examining is arranged. The released ATP therefore moves parallel to two paths to the regions where the reagent is present which, together with the ATP, results in a light-emitting sample. A reference is hereby created for the measurement result since a comparison between the total quantity of cells and the pathological cells is obtained on the basis of the difference between the two types of reagent initially used in the destruction of the cell walls.

This method is applied particularly to determine the degree of infection with mastitis of milk from milk-producing animals such as cows, sheep or goats. The carrier is provided here with guide means for guiding milk arranged on the carrier, for instance by dipping the carrier in milk, to a first position on the carrier at which a first reagent is present which, in contact with milk, emits light in accordance with the quantity of mastitis cells, and to a second position at which a first and a second reagent are present which, in contact with milk, emit a defined luminous flux. At the position where only the first reagent is present a first light source is thus formed with a light intensity which is determined by the quantity of mastitis cells, and at the position where both the first and second reagent are present a second light source is formed which has a light intensity which is formed by the quantity of mastitis cells and the reaction between the milk and the second reagent.

It will otherwise be apparent that the method according to the invention can also be applied for numerous other purposes of a biological or other nature.

The invention claimed is:

1. A device for detecting small quantities of light, comprising a first CCD or CMOS electronic image converter having a large number of light-sensitive cells for detecting photons representing the small quantities of light and for supplying a readout signal, and a processing circuit for processing the readout signal to a measurement signal representing the quantity of received photons, wherein the device comprises at least one second electronic image converter which is the same as the first electronic image converter and which is shielded from light;

the processing circuit is also connected to the second electronic image converter and is adapted to compensate the readout signal of the first electronic image converter with a readout signal of the second electronic image converter;

the first and the second image converters are thermally closely coupled to each other; and for each image converter, readout signals coming from any of the light sensitive cells of said image converter are respectively added together either by the processing circuit or by said image convertor for an adjustable period of time.

2. The device as claimed in claim 1, wherein the first and the second image converters are placed in the vicinity of each other.

3. The device as claimed in claim 1, wherein the light-sensitive cells present on each of the first and the second image converter are divided into a measurement group and a reference group, that the reference group is shielded from light and that the processing circuit is adapted to compensate readout signals of the light-sensitive cells belonging to the measurement group with readout signals of light-sensitive cells belonging to the reference group.

4. The device as claimed in claim 1, wherein the device comprises a third electronic image converter which is the same as the first and the second electronic image converters and which is adapted to receive light signals functioning as comparison;
   that the processing circuit is also connected to the third electronic image converter and is adapted to compare the readout signal of the first electronic image converter to the readout signal of the third electronic image converter; and
   that the first, second and third electronic image converters are thermally closely coupled to each other.

5. The device as claimed in claim 4, wherein the first, the second and the third electronic image converters are placed in the vicinity of each other.

6. The device as claimed in claim 4, wherein the light-sensitive cells present on the third image converter are divided into a measurement group and a reference group, that the reference group is shielded from light and that the processing circuit is adapted to compensate readout signals of the light-sensitive cells belonging to the measurement group with readout signals of light-sensitive cells belonging to the reference group.

7. The device as claimed in claim 1, wherein the device is provided with positioning means for positioning a carrier so that light emitted by light-emitting elements placed at a first position on the carrier reaches the first electronic image converter while excluding other light.

8. The device as claimed in claim 7, wherein the positioning means are adapted to position a carrier so that light emitted by light-emitting elements placed at a second position on the carrier reaches the third electronic image converter while excluding other light.

9. The carrier for carrying light-exciting samples, wherein the carrier is adapted to be positioned by the positioning means as claimed in claim 8.

10. A carrier for carrying light-exciting samples, wherein the carrier is adapted to be positioned by the positioning means as claimed in claim 7.

11. The carrier as claimed in claim 10, wherein the carrier is adapted to add at least a first reagent to the sample and that the first reagent is adapted to form a first light-emitting element together with cells of disease-causing micro-organisms present in the sample.

12. The carrier as claimed in claim 10, wherein the carrier is adapted to add at least a second reagent to the sample and that the second reagent is adapted to form a second light-emitting element together with cells of disease-causing micro-organisms present in the sample.

13. A method for detecting light-emitting elements present in a carrier, comprising the steps of mutually defined positioning of the carrier and a first electronic image converter, detecting the light emitted by the light-emitting elements present in the carrier, reading the first electronic image converter with a processing circuit connected to the first electronic image converter, and generating a first signal representing the number of photons received by the first electronic image converter within a period of time, wherein the first signal is compensated with a second signal coming from a second electronic image converter which is the same as the first electronic image converter and is shielded from light, but thermally closely coupled to the first electronic image converter.

14. The method as claimed in claim 13, wherein a biological sample is arranged on the carrier, the biological sample is brought into contact with a first reagent and a second reagent, that the combination of the first biological sample and the first reagent forms first light-emitting elements which are positioned relative to the first electronic image converter, and that the combination of the biological sample and the second reagent forms second light-emitting elements which are positioned relative to a third electronic image converter, and that the first signal and a third signal coming from the third electronic image converter are compensated with the second signal coming from a second electronic image converter which is the same as the first and third electronic image converters and is shielded from light, but thermally closely coupled to the first and third electronic image converters.

* * * * *

UNITED STATES PATENT AND TRADEMARK OFFICE
CERTIFICATE OF CORRECTION

PATENT NO. : 8,648,289 B2  
APPLICATION NO. : 12/743435  
DATED : February 11, 2014  
INVENTOR(S) : Pieter Tjerk Koopman Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 687 days.

Signed and Sealed this
Twenty-ninth Day of September, 2015

Michelle K. Lee
*Director of the United States Patent and Trademark Office*